United States Patent [19]
Hildebrand

[11] Patent Number: 5,335,184
[45] Date of Patent: Aug. 2, 1994

[54] NONDESTRUCTIVE ULTRASONIC TESTING OF MATERIALS

[75] Inventor: Bernard P. Hildebrand, Richland, Wash.

[73] Assignee: Battelle Memorial Institute, Richland, Wash.

[21] Appl. No.: 553,939

[22] Filed: Jul. 16, 1990

[51] Int. Cl.⁵ .............................. G06F 15/20
[52] U.S. Cl. .................. 364/507; 364/554; 73/577
[58] Field of Search ......... 364/507, 508, 498, 550, 364/551.01, 553, 554; 73/577, 599

[56] References Cited

U.S. PATENT DOCUMENTS

| | | | |
|---|---|---|---|
| 3,911,733 | 10/1975 | Bhuta et al. | 73/577 |
| 4,609,994 | 9/1986 | Bassim et al. | 73/577 |
| 4,764,970 | 8/1988 | Hayashi et al. | 364/507 |
| 4,794,545 | 12/1988 | Salvado | 364/507 |
| 4,866,614 | 9/1989 | Tam | 364/507 |
| 4,897,796 | 1/1990 | Salvado | 364/507 |

*Primary Examiner*—Parshotam S. Lall
*Assistant Examiner*—Ellis B. Ramirez
*Attorney, Agent, or Firm*—Stephen R. May

[57] ABSTRACT

Reflection wave forms obtained from aged and unaged material samples can be compared in order to indicate trends toward age-related flaws. Statistical comparison of a large number of data points from such wave forms can indicate changes in the microstructure of the material due to aging. The process is useful for predicting when flaws may occur in structural elements of high risk structures such as nuclear power plants, airplanes, and bridges.

10 Claims, 3 Drawing Sheets

NONDESTRUCTIVE ULTRASONIC TESTING OF MATERIALS

This invention was made with Government support under Contract DE-AC06-76RLO 1830 awarded by the U.S. Department of Energy. The Government has certain rights in the invention.

FIELD OF THE INVENTION

The present invention relates to the nondestructive testing of materials using ultrasonic pulses or waves. More particularly, the present invention relates specifically to the enhanced aging of a test material, with periodic ultrasonic testing, in order to determine susceptibility to failure-related flaws prior to installation of the material.

BACKGROUND OF THE INVENTION

Nondestructive testing of materials using ultrasonic waves in order to determine the presence of cracks, flaws, inclusions, etc., in, for instance, metallic structures, is well known to those skilled in the art. Such procedures are commonly utilized to test materials prior to their installation, or materials which have already been installed and in service for a period of time. For example, the ultrasonic testing of metallic objects used in fastening or structural components of aircraft may be accomplished prior to their installation. Likewise, nondestructive ultrasonic examination of such components may be performed after some substantial period of aging. In both cases, the nondestructive testing is intended to identify failure-inducing flaws prior to an actual failure.

Nondestructive testing with ultrasonic imaging is also utilized in the detection of diseased tissue, as in U.S. Pat. No. 4,817,015, Insana et al., wherein tissue signatures were obtained from first and second order statistics of an image texture in order to discriminate between normal and abnormal tissue conditions. The process characterized tissues by statistically comparing the back scatter properties of tissues estimated from wave form statistics resulting from the mean spacing of periodic tissue scatterers over the test tissue.

However, none of the prior art discloses a method for statistically determining the presence of aging-related conditions in a structure which are the precursors to failure-related flaws, such as cracks. In spite of the obvious usefulness of such a process, there has not been provided a method for accomplishing this result.

SUMMARY OF THE INVENTION

In its broadest embodiment, the method of the present invention is a procedure to detect conditions in a structure incident to aging which may form the basis for failure-related flaws at some later date. As used herein, the word "condition" can refer to any change in a structural attribute which is statistically identifiable, and which may indicate a propensity to evolve into a flaw with further aging. The term "flaw" is intended to mean any crack, void, change in crystalline structure, etc., which leads to a structural failure.

The method of the invention is a nondestructive testing procedure which either (a) identifies a characteristic of a material prior to installation of the material, or (b) identifies a change in a material already installed, which indicates the presence of conditions possibly resulting in failure-related flaws with further aging. The method statistically compares pre-aging with post-aging ultrasonic reflection wave forms of the material in order to detect changes, or trends in the microstructure of the material. An ultrasonic wave of a known frequency is introduced into the material prior to substantial aging of the material, and a reflection wave form of the material is generated and stored for later use. After aging, an ultrasonic wave of the same frequency is reintroduced into the material, and the reflection wave form of the aged material is statistically compared to the reflection image of the nonaged material. First and second order statistical comparisons of data derived from these wave forms at any given time will indicate microstructural changes in the material.

For the purposes of this invention, the word "aging" may mean any phenomenon which causes microstructural changes in a material over time. For instance, exposure of a material to high temperatures, radiation, torsional strains, and other like phenomena, may all be included within the term "aging".

It is an object of the present invention to provide a simple method of determining the propensity of a structural member to develop conditions which may result in failurerelated flaws, prior to the actual development of the condition.

DETAILED DESCRIPTION OF THE INVENTION

Age-induced microstructural changes in structural materials may result from any one of the large number of environmental insults. For example, long-term exposure to radiation, high heat, mechanical (torsional) stress, or tensile or vibrational stress may result in microstructural changes to, for example, a metallic structural element. Precipitation (the uniform precipitation of solutes in a solid solution, which when hardened, prevent dislocations from passing through), segregation and damage accumulation may all result from prolonged exposure to such stresses. It is presumed that with sufficient exposure, such stresses may lead to flaws in the structural element. Obviously, it would be advantageous to identify a potential flaw before it actually developed and caused serious damage. While the potential application of the apparatus of the present invention is virtually unlimited, applicant has identified a number of high-risk situations for immediate application in nuclear power plants, bridges, buildings, and aviation, to name only a few.

Figure 1:
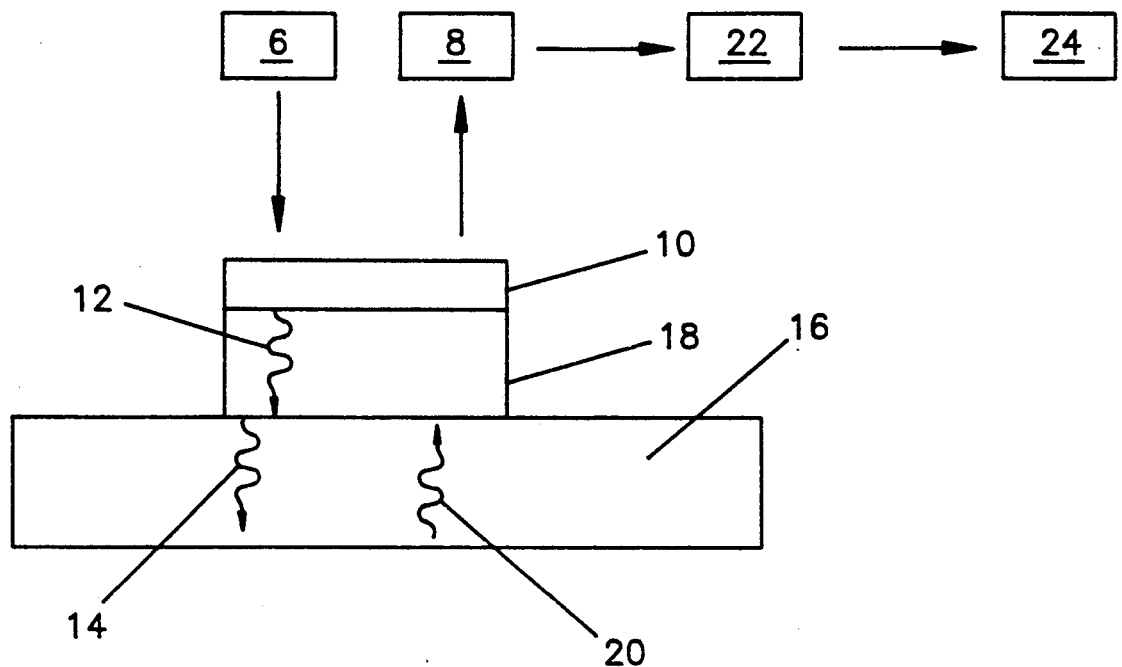
FIG. 1 is a schematic diagram of an apparatus to practice the method of the present invention.

The method of the present invention is carried out as illustrated schematically in FIG. 1. A pulser 6 is selected to produce an ultrasonic pulse 12 of a particular frequency after being formed by transducer 10. The input wave form 14 is introduced onto the surface of material 16 through a coupling medium 18. The transducer 10 and coupling medium 18 are of conventional design, and are well known to those skilled in this art. A reflection wave form 20 of the input wave 14 is reflected from the material 16 to the coupling medium 18 and is received in receiver 8 and stored in an analog-to-digital converter 22. A statistical comparison 24 is performed on the reflection wave forms 20 of materials 16 prior to and after aging. While it is believed that the present invention will find particular application in the testing of metallic materials 16, it is believed that it will be equally sensitive to changes in non-metallic materials, such as plastics, composites, etc.

Figure 2:
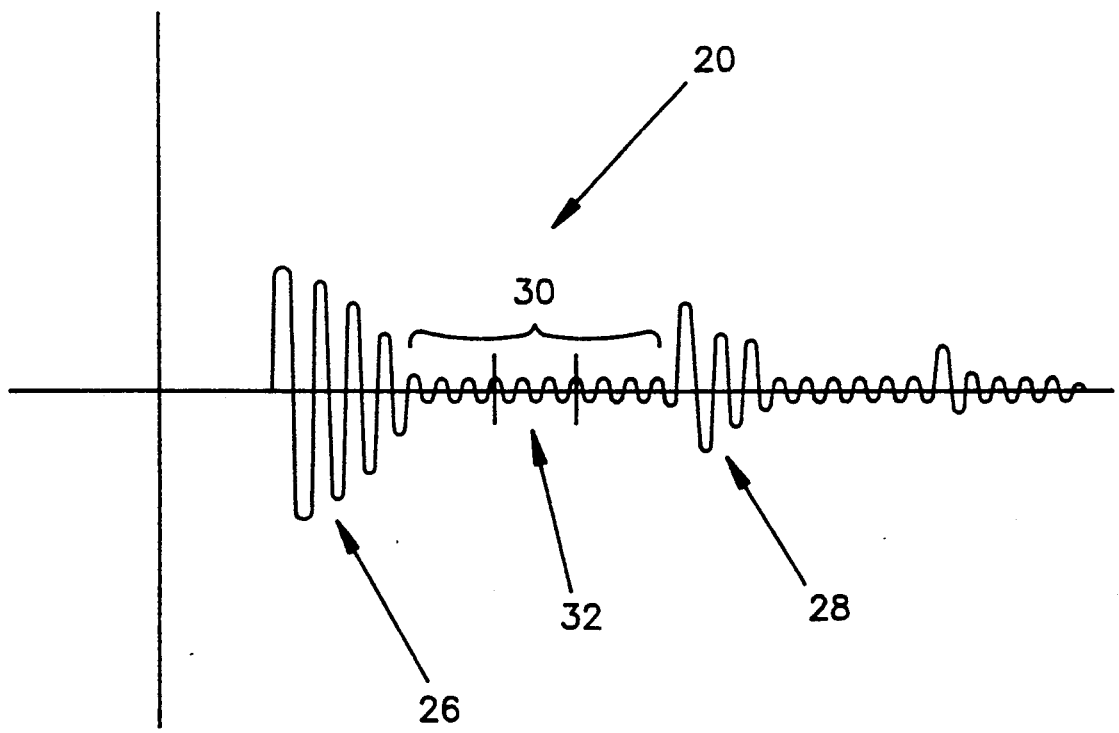
FIG. 2 is a representative reflection wave form analyzed by the method of the present invention.

Rather than store an entire reflection wave form 20, it has been found that use of only a small portion of the reflection wave form is adequate. As illustrated in FIG. 2, the reflection wave form 20 illustrates a spectrum having large peaks for reflectance 26 and 28 from the top surface of the material 16 and from the bottom surface, respectfully. That portion 30 between the peaks 26, 28, which has heretofore been referred to as noise, is actually a representation of the scattering of the ultrasonic wave in the material due to the microstructure of the material. It has been found that as, for example, crystalline changes occur in metallic materials, the noise pattern 30 also changes. Therefore, a small portion, or "gate" 32 of the noise is stored at 22 as an indicator of the microstructure of the material.

The ultrasonic wave 12 produced by transducer 10 may be tuned to produce reflection wave forms 20 as desired. It is believed that relatively narrow beam diameters (less than ¼") producing sharper wave forms, are preferred. It is preferred to generate a large number of closely spaced data points so as to increase the density of observations to permit detection of small perturbations. While many different indicia may be utilized to compare the aged versus nonaged reflection wave forms of FIG. 2, applicant has chosen to utilize the single greatest "peak" within the gate 32 as indicative of the characterization of the microstructure of the material at that point. It is to be understood that the significance of the individual peak chosen within the gate 32 is not the absolute magnitude of the peak, but rather the magnitude of the peak relative to each of the other data points collected.

There are a large number of different statistical measures that may be utilized in comparing aged versus nonaged data. As examples of first order statistics which may be useful in the process of the present invention, one or more of the following may be utilized: average, mode, variance, standard error, kurtosis, S/N ratio, median, geometric mean, standard deviation, skewness and coefficient of variation. Second order statistics include, but are not limited to, correlation coefficient, students t, snedecors F, chi-square, and R. While each of the statistical analyses may be performed by hand, it is most efficient to perform such calculations with a computer.

The greater the number of data points collected per unit area, the more useful is the process of the present invention in predicting microstructural changes in the reference material.

The ultrasonic noise, or back scatter, analyzed in the gate 32 is affected by a variety of different attributes of the reference material. Factors such as grain size, grain size distribution, dislocation density, texture, inclusions, voids, and residual stress all contribute to the unique reflection image. However, because the comparison utilized in this invention is a relative determination, such factors should be zeroed out.

The process of the present invention may be more easily understood with reference to the following example.

EXAMPLE

Test specimens measuring 1 inch by inch or 2 inches by 2 inches were cut from a plate of 0.36 inch thick 304 stainless steel. A portion of the specimens were heated in a furnace at various temperatures up to 700° C. for periods of 1, 15, 25, and 100 hours. The heat treatment enhanced the aging conditions of the samples in order to accelerate aging. Ten thousand ultrasonic measurements were taken on each sample.

Microstructural characterization of the stainless steel samples was as follows:
1. Grain size
40 micron (mill annealed)
110 micron (solution annealed)
2. Transmission electron microscopy—no carbides in solution annealed samples Carbide volume fraction increased with heat treatment time—intergranular carbides predominate after aging for short time periods, some intragranular carbides appear after long aging periods.
3. Degree of sensitization/IGSCC susceptibility—moderate levels up to aging for 10 hours at 700° C.

Severely sensitized after 25 to 100 hours of aging at 700° C.

Desensitization begins after about 75 hours at 700° C.
4. X-Ray diffraction—no change in texture with any level of heat treatment aging.

Figure 3:
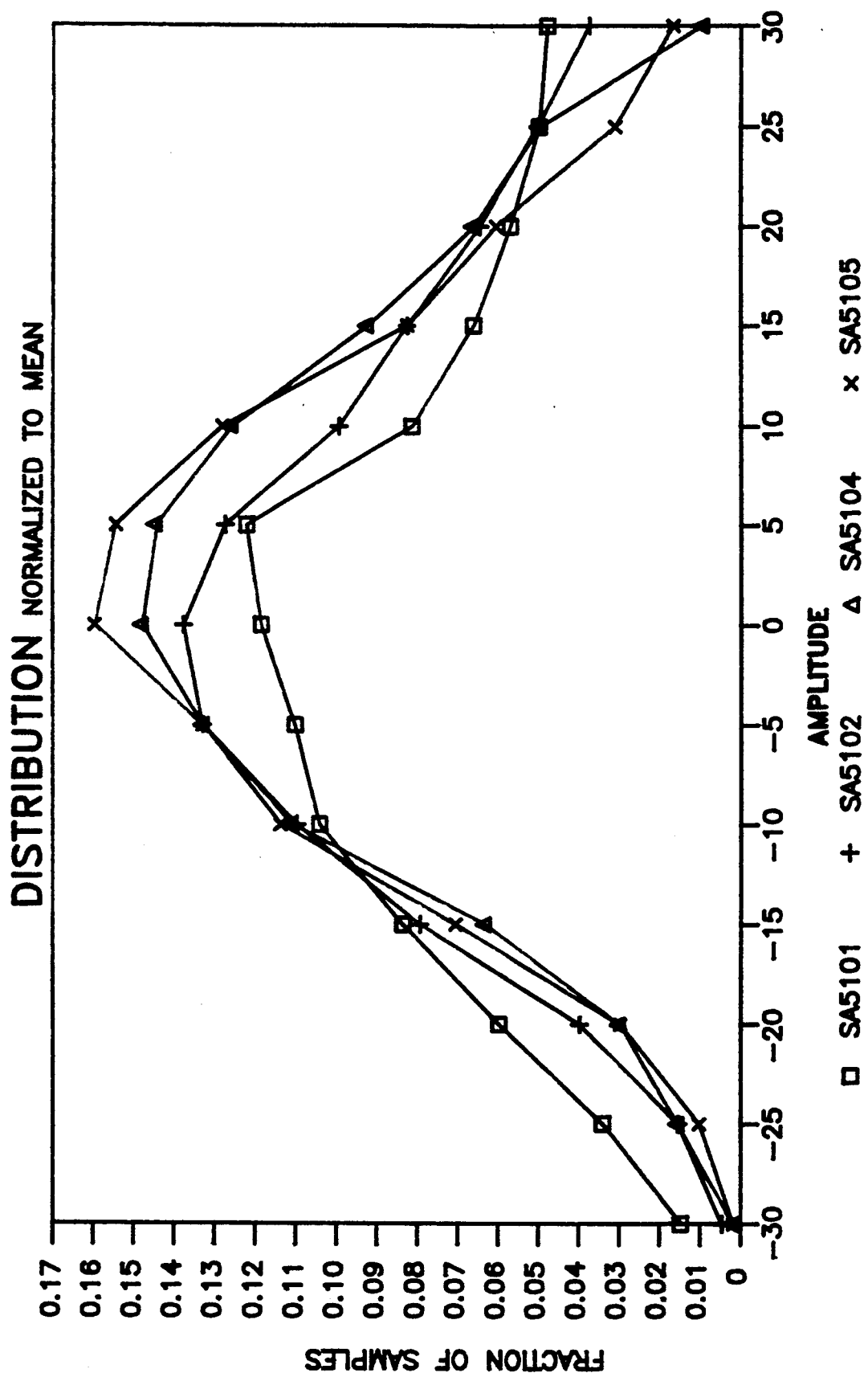
FIG. 3 is a graphic illustration of a size distribution (normalized to mean) of peak amplitude of reflection wave forms.
Figure 4:
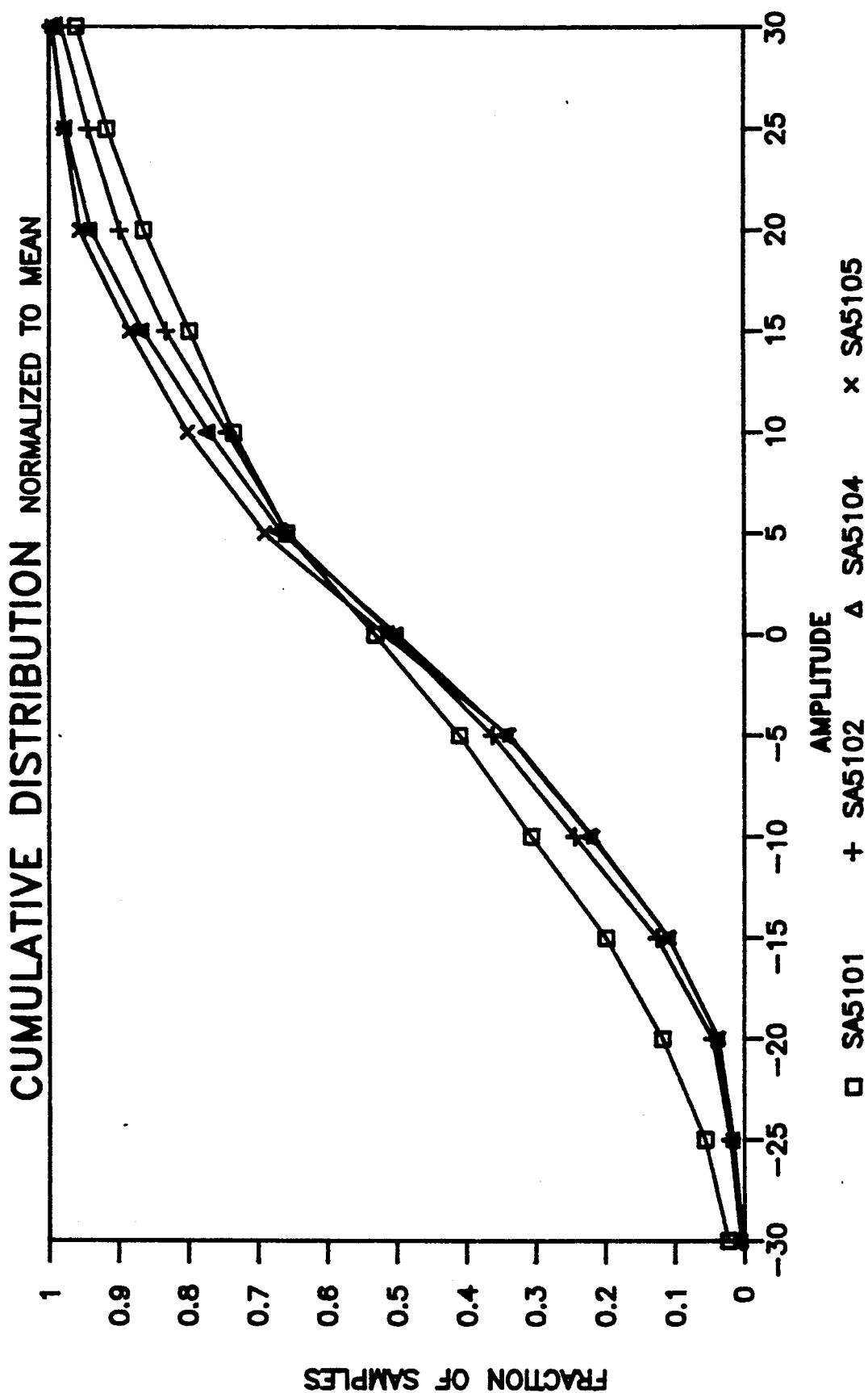
FIG. 4 is a graphic illustration of a cumulative distribution of peak amplitude of reflection wave forms.

Distribution of the peak amplitudes, normalized to mean, followed the distribution illustrated in FIG. 3. The cumulative distribution, normalized to mean, of the peak amplitude is illustrated in FIG. 4.

Comparisons of several statistical measurements illustrate the usefulness of the present invention. When comparing the aged sample to the nonaged sample, Average amplitude increased by 50%.

Ratio of maximum to average amplitude decreased by 32%.

Ratio of average to standard deviation of amplitude increased by 76%.

Ratio of amplitude at 50% population point to amplitude at 75% population point decreased by 52% 2.85 to 1.35).

These statistical measurements indicate that microstructural changes, related to aging of a given material, can be observed ultrasonically prior to a failure of the material and prior to a flow actually occuring. This process may have special application to those situations where detection of a potential failure, even before aging-related flaws occur, can avert a catastrophic accident.

While the invention has been described herein with reference to specific embodiments, it is to be understood that the scope of this invention is to be limited solely with reference to the appended claims.

I claim:

1. A method of detecting changes in a material between a top surface and a bottom surface due to aging, comprising the steps of:
   (a) introducing an ultrasonic wave of a known frequency into a material to be tested prior to substantial aging of the material, such that a reflection wave form of the ultrasonic wave passing from one surface through the material to the other surface is generated and stored;

(b) periodically passing an ultrasonic wave of the same frequency as in above from one surface through the material to the other surface at various periods of aging and retrieving and storing the reflection wave form of the ultrasonic wave passed through the aged material; and (c) statistically comparing the reflection wave form generated in (a) with the reflection wave form generated in (b) above in order to determine structural changes in the material.

2. The method as set forth in claim 1, wherein said method is a method for the nondestructive testing of a material prior to its installation.

3. The method as set forth in claim 2, wherein aging of the material is artificially enhanced prior to installation of the material such that the statistical comparison may be performed prior to installation.

4. The method as set forth in claim 1, wherein the material comprises stainless steel.

5. The method as set forth in claim 4, wherein the frequency of the ultrasonic wave is between from about 1 to about 100 megahertz (MHz).

6. The method as set forth in claim 5, wherein the frequency is from about 1 to about 10 MHz.

7. The method as set forth in claim 1, further comprising generating statistical analyses of the reflection wave forms of steps (a) and (b), wherein the analyses comprise at least one of the following:

average amplitude of feedback signals in a given area of the reflection image, ratio of maximum amplitude to average amplitude in the given area, ratio of average amplitude to standard deviation of amplitudes, and ratio of amplitude that a 50% population location to the amplitude at a 75% population location.

8. The method as set forth in claim 1, wherein the analyses are performed on a test material prior to installation of the material such that an aging-related flaw may be predicted prior to installation of the material.

9. A method of detecting changes in a material due to aging, comprising the steps of:

(a) introducing an ultrasonic wave having a frequency of from about 1 to about 100 MHz into a material to be tested at a plurality of locations on the material, at a time prior to substantial aging of the material;

(b) recording a reflection wave form of the ultrasonic wave at each of the plurality of locations;

(c) introducing an ultrasonic wave of the same frequency as in (a) above into the same material at a time after aging of the material has occurred, and recording a reflection wave form of said wave;

(d) statistically comparing the reflection wave form of (b) to the reflection wave form of (c) by
   (i) deflecting a minor portion of the reflection wave form in each of (a) and (b) above, between a front and back surface reflection for each of the plurality of locations,
   (ii) determining the peak signal in the minor portion of each of the plurality of locations, and
   (iii) comparing the peak signals of each of the plurality of locations to one another to determine changes in the peak signals for at least one period of aging of the material; and (e) detecting a difference in the reflection wave forms of steps (b) and (c) above by the statistical comparison of step (d), as an indication of changes in the structure of the material resulting from aging.

10. A method of nondestructive testing to predict changes in a material due to aging, comprising the steps of:

(a) passing an ultrasonic wave of a known freuqency through an upper surface of the material to a lower surface of the material to be tested prior to substantial aging of the material, such that a reflection wave form of the ultrasonic wave passing through the material is generated and stored;

(b) subjecting the material to enhanced aging conditions in order to accelerate the aging of the material;

(c) periodically passing an ultrasonic wave through the material during the enhanced aging conditions at the same freuqency as in (a) above and retrieving and storing a reflection wave form of the ultrasonic wave; and (d) statistically comparing the reflection wave from generated in (a) and (c) in order to determine structural changes in the material prior to the formation of failurerelated flaws.

* * * * *

UNITED STATES PATENT AND TRADEMARK OFFICE
CERTIFICATE OF CORRECTION

PATENT NO. : 5,335,184
DATED : August 2, 1994
INVENTOR(S) : Bernard P. Hildebrand It is certified that error appears in the above-indentified patent and that said Letters Patent is hereby corrected as shown below:

In column 4, line 45, after "52%", please insert --(from--.
In column 5, line 2, after the word "in", please insert --(a)--.

Signed and Sealed this

Twenty-fifth Day of June, 1996

Attest:

BRUCE LEHMAN

Attesting Officer     Commissioner of Patents and Trademarks